(12) United States Patent
Huang et al.

(10) Patent No.: US 10,730,042 B2
(45) Date of Patent: Aug. 4, 2020

(54) BIOLOGICAL DETECTION SYSTEM

(71) Applicant: CE Biotechnology, Inc., Apia (WS)

(72) Inventors: Chung-Er Huang, Apia (WS);
Sheng-Wen Chen, Apia (WS);
Hsin-Cheng Ho, Apia (WS);
Wei-Cheng Hsu, Apia (WS); Ming Chen, Apia (WS)

(73) Assignee: CE Biotechnology, Inc., Apia (WS)

( * ) Notice: Subject to any disclaimer, the term of this patent is extended or adjusted under 35 U.S.C. 154(b) by 355 days.

(21) Appl. No.: 15/861,266

(22) Filed: Jan. 3, 2018

(65) Prior Publication Data

US 2019/0001320 A1    Jan. 3, 2019

(30) Foreign Application Priority Data

Jun. 30, 2017  (TW) .............................. 106121904 A

(51) Int. Cl.
*B01L 3/00* (2006.01)
*G01N 27/447* (2006.01)
(Continued)

(52) U.S. Cl.
CPC ......... *B01L 3/502* (2013.01); *B01L 3/502753* (2013.01); *G01N 15/1031* (2013.01); *G01N 15/1056* (2013.01); *G01N 15/1484* (2013.01); *G01N 27/44791* (2013.01); *G01N 33/5438* (2013.01); *B01L 2200/0647* (2013.01);
(Continued)

(58) Field of Classification Search
CPC ............... B01L 3/502; B01L 3/502753; B01L 2300/0877; B01L 2200/0647; B01L 2300/0896; B01L 2400/086; B01L 2300/0645; B01L 2400/0424; B01L 2300/0819; B01L 2200/12; B01L 3/5027; B01L 3/50273; G01N 15/1484; G01N 33/5438; G01N 27/44791; G01N 15/1031;
(Continued)

(56) References Cited

U.S. PATENT DOCUMENTS

2006/0160243 A1* 7/2006 Tang .................... G01N 1/40
436/177
2007/0161051 A1* 7/2007 Tsinberg .............. G01N 1/2813
435/7.2
(Continued)

OTHER PUBLICATIONS

Wang et al., Highly efficient capture of circulating tumor cells by using nanostructured silicon substrates with integrated chaotic micromixers, 2011, Wiley, Cell Capture, PP3084-3088. (Year: 2011).*
Liu et al., "Fabrication and photocatalytic properties of silicon nanowires by metal-assisted chemical etching: effect of $H_2O_2$ concentration", Nanoscale Research Letters 2012, 7:663.
(Continued)

*Primary Examiner* — David C Mellon
(74) *Attorney, Agent, or Firm* — Fish & Richardson P.C.

(57) ABSTRACT

A biological detection system for detecting a liquid sample containing a plurality of target biological particles includes a capturing device including a cell structure, an inlet, an outlet, a monolithic chip, and a layer of binding agent. The monolithic chip includes a substrate and a plurality of discrete nano-sized structures which are displaced from each other and each of which extends uprightly from the substrate to terminate at a top end. The layer of binding agent is formed on the top end of each of the discrete nano-sized structures for capturing the target biological particles.

19 Claims, 9 Drawing Sheets

(51) Int. Cl.
  *G01N 15/10*    (2006.01)
  *G01N 15/14*    (2006.01)
  *G01N 33/543*   (2006.01)
  *B03C 5/02*     (2006.01)
  *B03C 5/00*     (2006.01)

(52) U.S. Cl.
  CPC ... *B01L 2200/12* (2013.01); *B01L 2300/0645* (2013.01); *B01L 2300/0819* (2013.01); *B01L 2300/0877* (2013.01); *B01L 2300/0896* (2013.01); *B01L 2400/0424* (2013.01); *B01L 2400/086* (2013.01); *B03C 5/005* (2013.01); *B03C 5/026* (2013.01); *G01N 2015/1006* (2013.01); *G01N 2015/1486* (2013.01)

(58) Field of Classification Search
  CPC ....... G01N 15/1056; G01N 2015/1486; G01N 2015/1006; B03C 5/026; B03C 5/005
  See application file for complete search history.

(56) References Cited

U.S. PATENT DOCUMENTS

| | | | |
|---|---|---|---|
| 2011/0117577 A1* | 5/2011 | Reboud | B01L 3/502761 435/7.23 |
| 2011/0294187 A1* | 12/2011 | Toner | B01L 3/502761 435/177 |
| 2012/0003711 A1 | 1/2012 | Tseng et al. | |
| 2015/0285717 A1* | 10/2015 | Tseng | G01N 33/56966 435/7.21 |
| 2015/0285808 A1* | 10/2015 | Nagrath | G01N 33/54366 435/7.23 |
| 2017/0299495 A1 | 10/2017 | Huang et al. | |

OTHER PUBLICATIONS

Liu Y. et al. "Fabrication and photocatalytic properties of silicon nanowires by metal-assisted chemical etching: effect of H2O2 concentration" Nanoscale Research Letters 2012, 7:663.

* cited by examiner

BIOLOGICAL DETECTION SYSTEM

CROSS-REFERENCE TO RELATED APPLICATION

This application claims priority of Taiwanese Application No. 106121904, filed on Jun. 30, 2017.

FIELD

The disclosure relates to a biological detection system, and more particularly to a biological detection system adapted for detecting a liquid sample containing a plurality of target biological particles.

BACKGROUND

Applicant's co-pending U.S. patent application Ser. No. 15/469,111, which corresponds to Taiwanese Patent No. 539051, discloses a biological particle capturing and retrieving system which includes a capturing device and a retrieving device. The capturing device includes a substrate and an isolating layer. The isolating layer is disposed on the substrate, and includes a top surface and a plurality of fluidic grooves indented from the top surface. Each of the fluidic grooves has a bottom surface. The isolating layer further includes a plurality of pores formed in the bottom surface of each of the fluidic grooves. Each of the pores is adapted for capturing a corresponding one of the biological particles.

The retrieving device is used for retrieving the biological particles captured in the pores, and includes a micropipette having a tip member and a carrier which is attached to the tip member and which has an outer surface coated with a biological particle-binding material. When the tip member of the micropipette is moved close to one of the pores, the carrier binds with and retrieves the biological particle received in the one of the pores.

US 2012/0003711 discloses a microfluidic device for capturing biological cells. The microfluidic device comprises a substrate including a nanostructured surface region, a flow layer attached to the substrate to form a microfluidic channel, and a plurality of binding agents attached to the nanostructured surface region of the substrate. The nanostructured surface region is formed without use of a layer of photoresist.

An article entitled "Fabrication and photocatalytic properties of silicon nanowires by metal-assisted chemical etching: effect of $H_2O_2$ concentration" by Yousong Liu et al. in *Nanoscale Research Letters* 2012, 7:663 discloses preparation of monocrystalline silicon nanowire arrays through a metal-assisted chemical etching method of silicon wafers in an etching solution composed of HF and $H_2O_2$.

SUMMARY

An object of the disclosure is to provide a biological detection system adapted for detecting a liquid sample containing a plurality of target biological particles. The detection system includes a capturing device by which the target biological particles may be effectively captured and from which the captured target biological particles may be easily separated for subsequent further processing.

According to the disclosure, there is provided a biological detection system adapted for detecting a liquid sample containing a plurality of target biological particles. The biological detection system comprises a capturing device which includes a cell structure, an inlet, an outlet, a monolithic chip, and a layer of binding agent.

The cell structure includes a lower cell body and an upper cell body.

The lower cell body has a lower major surface and a lower adjoining surface. The lower adjoining surface is opposite to the lower major surface in a transverse direction and has a lower recess which extends downwardly to terminate at an inner floor surface and which includes an upper sub-recess configured to permit passage of the liquid sample and a lower sub-recess.

The upper cell body has a top major surface and an upper adjoining surface. The upper adjoining surface is opposite to the top major surface in the transverse direction, and has an upper recess extending toward the top major surface to terminate at a ceiling surface and configured to permit passage of the liquid sample.

The inlet is disposed upstream of the lower recess for introducing the liquid sample into the upper sub-recess of the lower recess.

The outlet is disposed downstream of the lower recess and is opposite to the inlet in a longitudinal direction.

The monolithic chip is configured to be matingly fitted in the lower sub-recess, and includes a substrate and a plurality of discrete nano-sized structures which are displaced from each other in the longitudinal direction and each of which extends uprightly from the substrate to terminate at a top end.

The layer of binding agent is formed on the top end of each of the discrete nano-sized structures for capturing the target biological particles.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Figure 1:
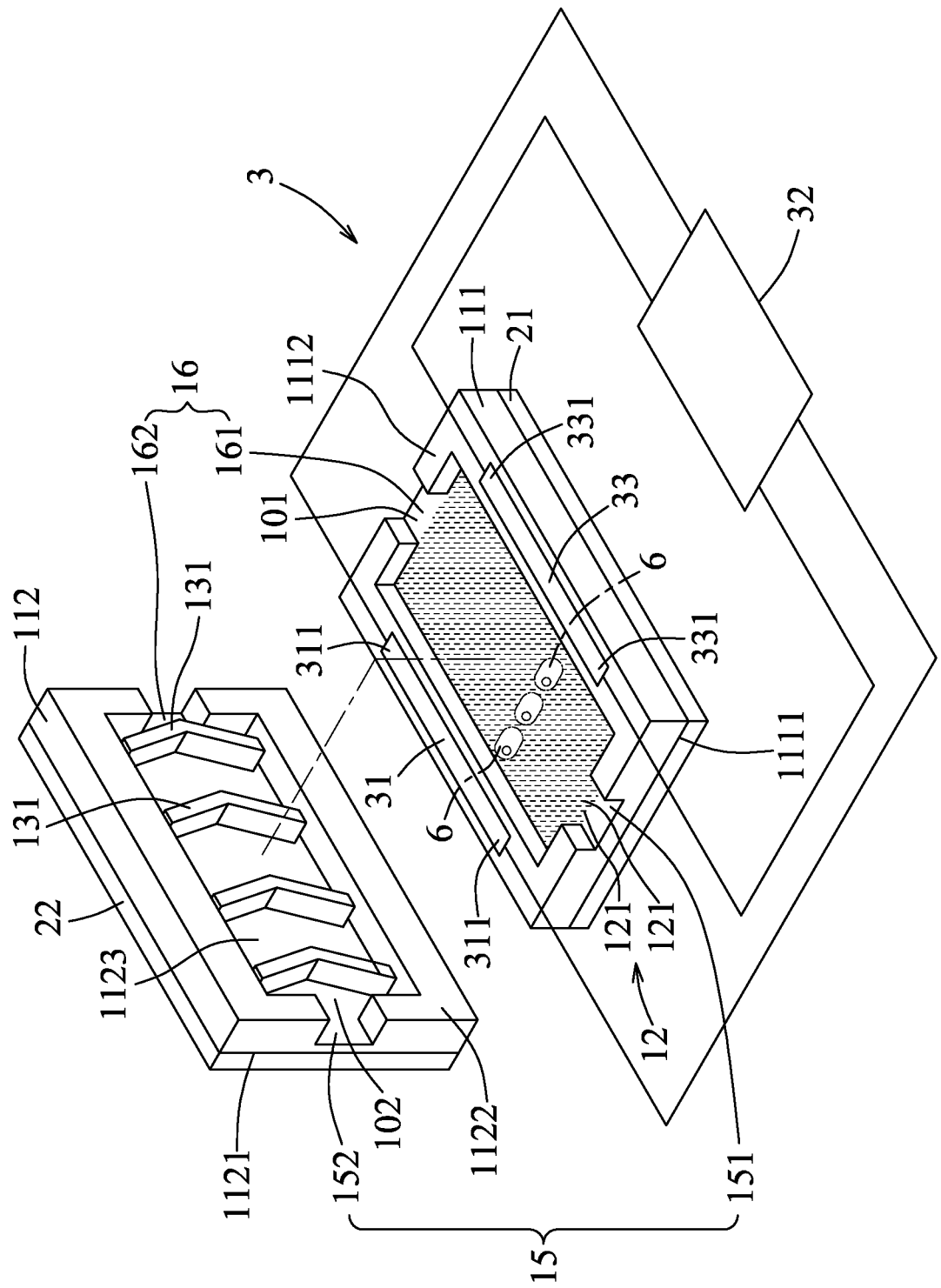
FIG. 1 is a schematic perspective view of a first embodiment of a biological detection system according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIGS. 1, 2, 3, and 4, a first embodiment of a biological detection system according to the present disclosure is adapted for detecting a liquid sample containing a plurality of target biological particles 6, and comprises a capturing device 1, an electrode unit 2, a separating device 5, and a signal measuring module 3.

The liquid sample, such as blood, lymph, urine, saliva, etc., may be obtained from an animal subject or a human subject. The target biological particles 6 may be, for example, cells, microorganisms, proteins, such as circulating tumor cells (CTCs), fetal nucleated red blood cells (fNRBCs), trophoblast, viruses, bacteria, antigens, etc. Alternatively, the target biological particles may be obtained from plants, for example, tissue extracts from plants.

The capturing device 1 is used for capturing the target biological particles 6, and includes a cell structure 11, an inlet 15, an outlet 16, a monolithic chip 12, and a layer of binding agent 123.

The cell structure 11 includes a lower cell body 111 and an upper cell body 112 which cooperate with each other to define a fluid passage 10.

The lower cell body 111 has a lower major surface 1111 and a lower adjoining surface 1112. The lower adjoining surface 1112 is opposite to the lower major surface 1111 in a transverse direction, and has a lower recess 101 which extends downwardly to terminate at an inner floor surface 1113 and which includes an upper sub-recess 1011 configured to permit passage of the liquid sample and a lower sub-recess 1012.

The upper cell body 112 has a top major surface 1121 and an upper adjoining surface 1122. The upper adjoining surface 1122 is opposite to the top major surface 1121 in the transverse direction, and has an upper recess 102 extending toward the top major surface 1121 to terminate at a ceiling surface 1123 and configured to permit passage of the liquid sample. The upper recess 102 and the lower recess 101 cooperate with each other to constitute the fluid passage 10.

The inlet 15 is disposed upstream of the lower recess 101 for introducing the liquid sample into the upper sub-recess 1011 of the lower recess 101, and includes a lower inlet half 151 and an upper inlet half 152. The lower inlet half 151 is formed in the lower cell body 111. The upper inlet half 152 is formed in the upper cell body 112 and is configured to be mated with the lower inlet half 151.

The outlet 16 is disposed downstream of the lower recess 101 and is opposite to the inlet 15 in a longitudinal direction. The outlet 16 includes a lower outlet half 161 formed in the lower cell body 111, and an upper outlet half 162 formed in the upper cell body 112 and configured to be mated with the lower outlet half 161.

The upper cell body 112 further has a plurality of baffles 131 disposed on the ceiling surface 1123 and displaced from each other in the longitudinal direction to deflect the flow stream of the liquid sample. The plurality of baffles 131 are arranged in a herringbone pattern so as to result in a turbulent effect for the liquid sample in the fluid passage 10.

The lower cell body 111 is made from a material which may be the same as or different from that for making the upper cell body 112. Each of the lower cell body 111 and the upper cell body 112 is independently made from a semiconducting material, a biologically compatible material, or the combination thereof, which are further described below.

Figure 2:
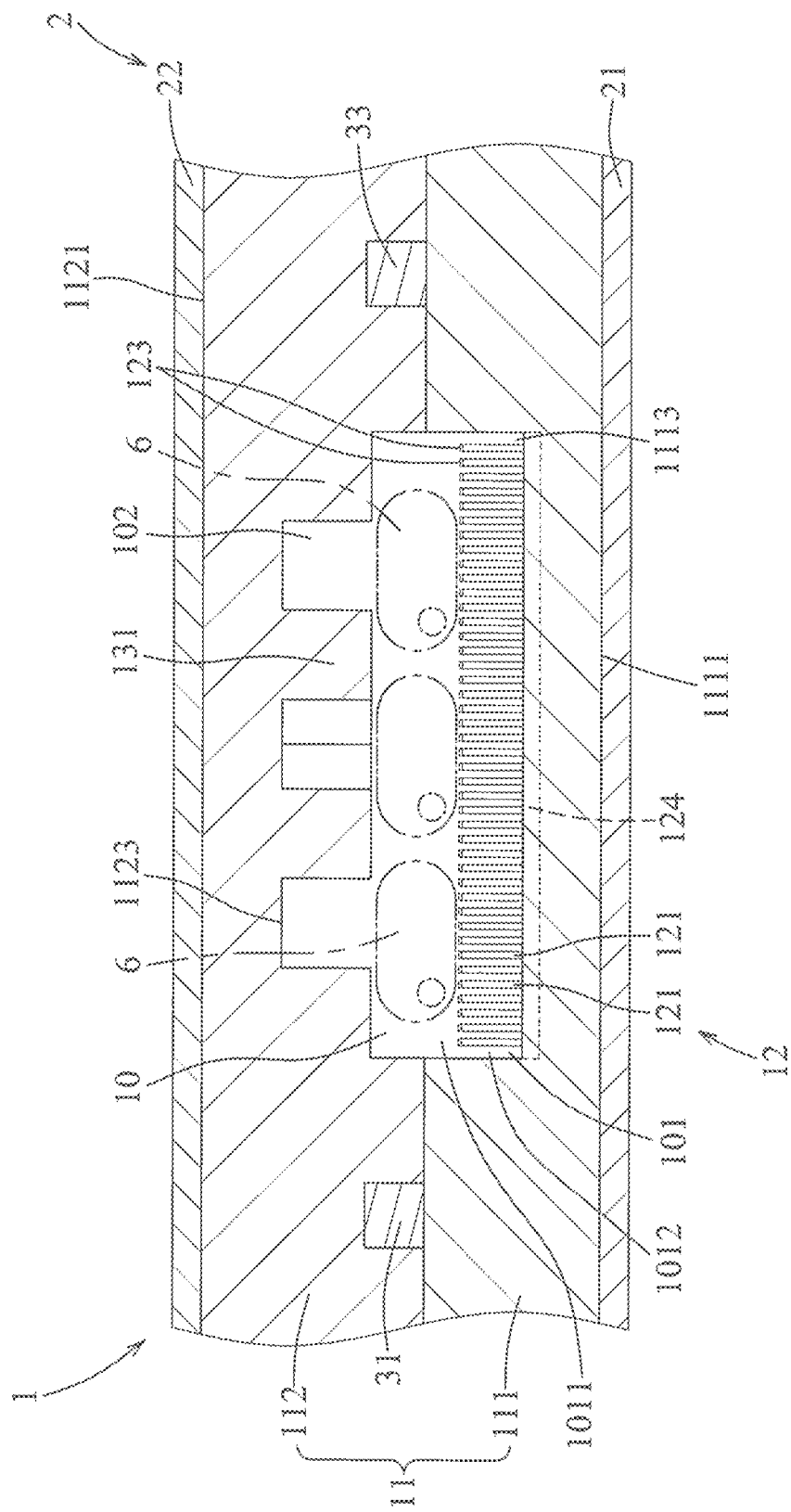
FIG. 2 is a partially sectional view of the first embodiment.
Figure 3:
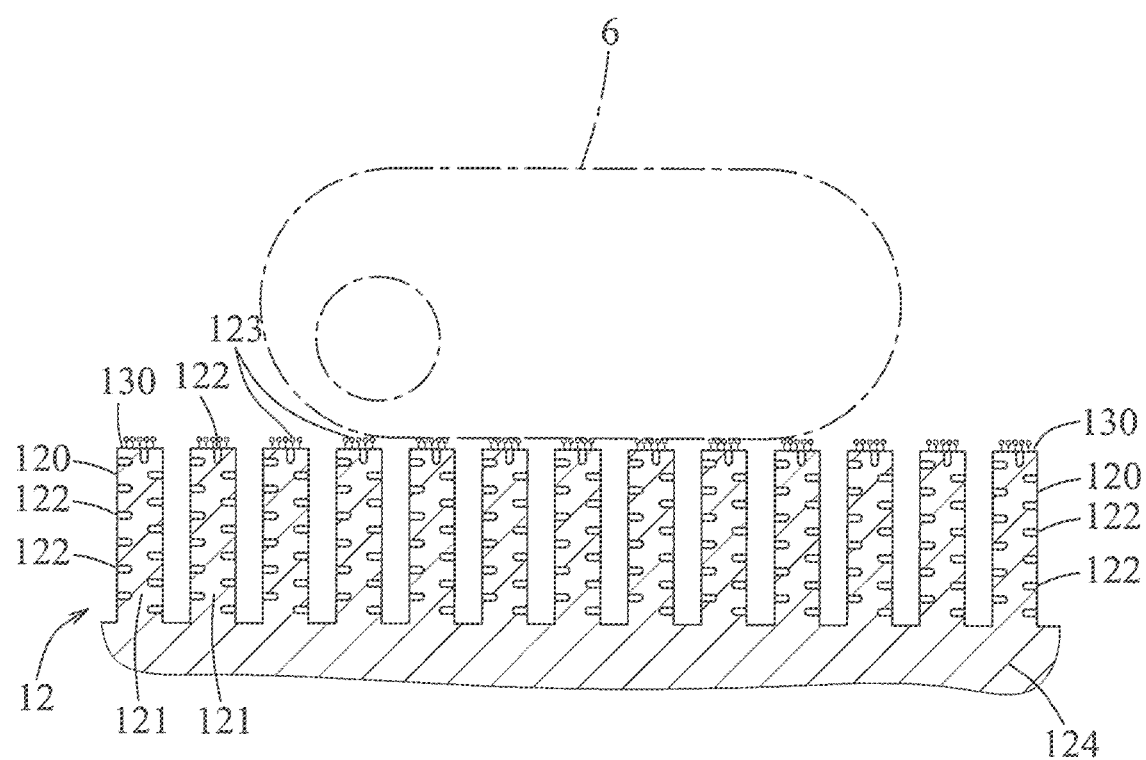
FIG. 3 is a schematic sectional view of a monolithic chip of a capturing device included in the first embodiment.

Specifically referring to FIGS. 2 and 3, the monolithic chip 12 is configured to be matingly fitted in the lower sub-recess 1012, and includes a substrate 124 and a plurality of discrete nano-sized structures 121 (e.g., "nano-on-nano structures") which are displaced from each other in the longitudinal direction and each of which extends uprightly from the substrate 124 to terminate at a top end 130.

The discrete nano-sized structures 121 are arranged in array. Each of the discrete nano-sized structures 121 is formed as a post-like configuration. In the embodiment, the monolithic chip 12 is formed integrally with the lower cell body 111.

The discrete nano-sized structures 121 are formed by a process including steps of:

a) providing an etchable layer on the substrate 124;

b) masking a plurality of areas on the etchable layer, each of the areas corresponding to the top end 130 of each of the discrete nano-sized structures 121; and c) etching a plurality of unmasked areas of the etchable layer downwardly toward the substrate 124 so as to form the discrete nano-sized structures 121.

Specifically, step b) includes sub-steps of:

b1) applying a layer of photoresist onto the etchable layer;

b2) subjecting the layer of the photoresist to radiation exposure via a patterned mask and to development (i.e. via a photolithographic technique) to form a patterned layer of the photoresist on the etchable layer so as to define the unmasked areas on which the photoresist is not provided;

b3) forming a layer of silver catalyst on the unmasked areas; and b4) lifting off the patterned layer of the photoresist to leave the silver catalyst on the unmasked areas of the etchable layer.

Specifically, step c) includes sub-steps of:

c1) immersing the etchable layer obtained in sub-step b4) in an etchant aqueous solution containing HF and $H_2O_2$ to subject the unmasked areas of the etchable layer to a silver-catalyzed chemical etching reaction which etches downwardly toward the substrate 124 to form the discrete nano-sized structures having a weakened mechanical strength as a result of a concurrent lateral etching; and c2) removing the silver catalyst from the etchable layer.

The etchable layer may be made from a material selected from the group consisting of a semiconducting material, a biologically compatible material, and a combination thereof. A non-limiting example of the semiconducting material is a silicon material, such as a silicon wafer. Examples of the biologically compatible material include, but are not limited to, polydimethylsiloxane, polymethyl methacrylate, polycarbonate, and combinations thereof. In the embodiment, the etchable layer is formed integrally with the substrate 124.

Specifically referring to FIG. 3, each of the discrete nano-sized structures 121 is shown to have an exterior surface 120 which extends between the top end 130 and the substrate 124 and which is formed with a plurality of pores 122 as a result of the concurrent lateral etching so as to permit each of the discrete nano-sized structures 121 to have the weakened mechanical strength. The pores 122 are also formed in the top end 130 of each of the discrete nano-sized structures 121. Each of the pores 122 has a size ranging from 500 pm to 50 nm. Each of the discrete nano-sized structures 121 has a width of at most 2 μm and an aspect ratio of at least 5. Each of the discrete nano-sized structures 121 has a porosity from 30 to 50% and a specific surface area from 200 to 800 $m^2/cm^3$. Induced charges having a charge state opposite to that of the charges carried on the target biological particles 6 may be generated and gathered on the surface of each of the discrete nano-sized structures 121 as a result of such a high specific surface area so that the target biological particles 6 may be attracted and captured by the discrete nano-sized structures 121 more effectively.

Figure 8:
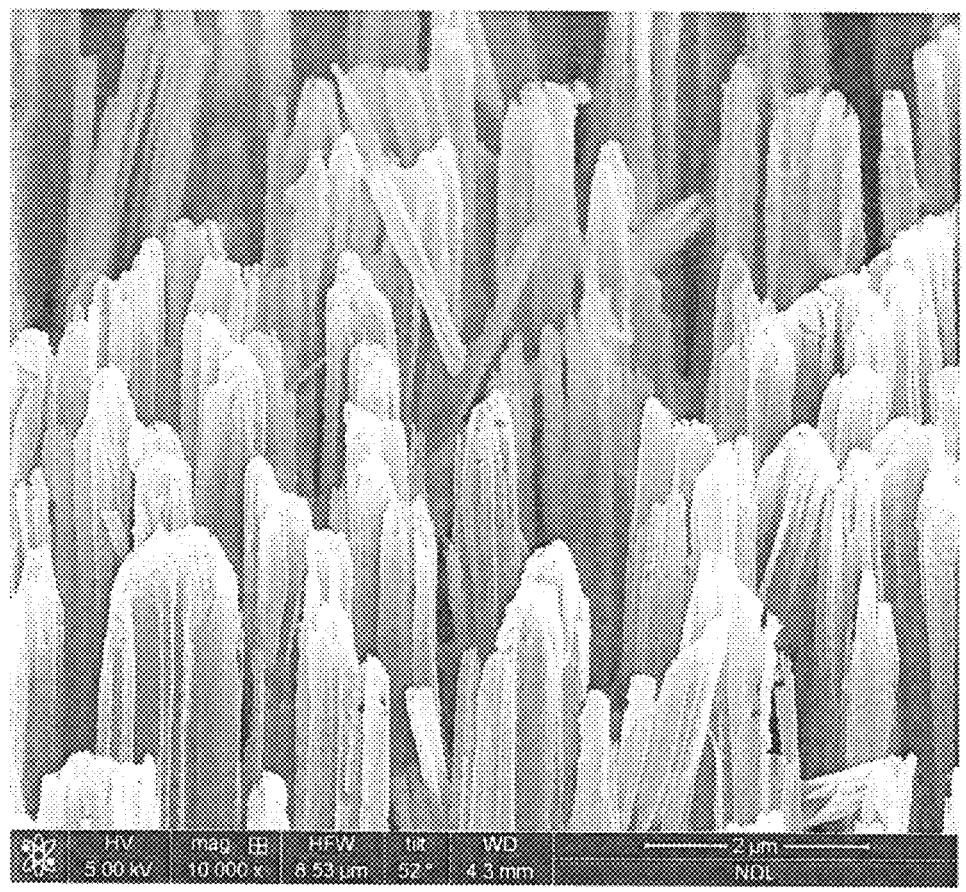
FIG. 8 is a scanning electron microscope (SEM) image (10,000×) of the discrete nano-sized structures formed in the first embodiment of a biological detection system according to the disclosure.
Figure 9:
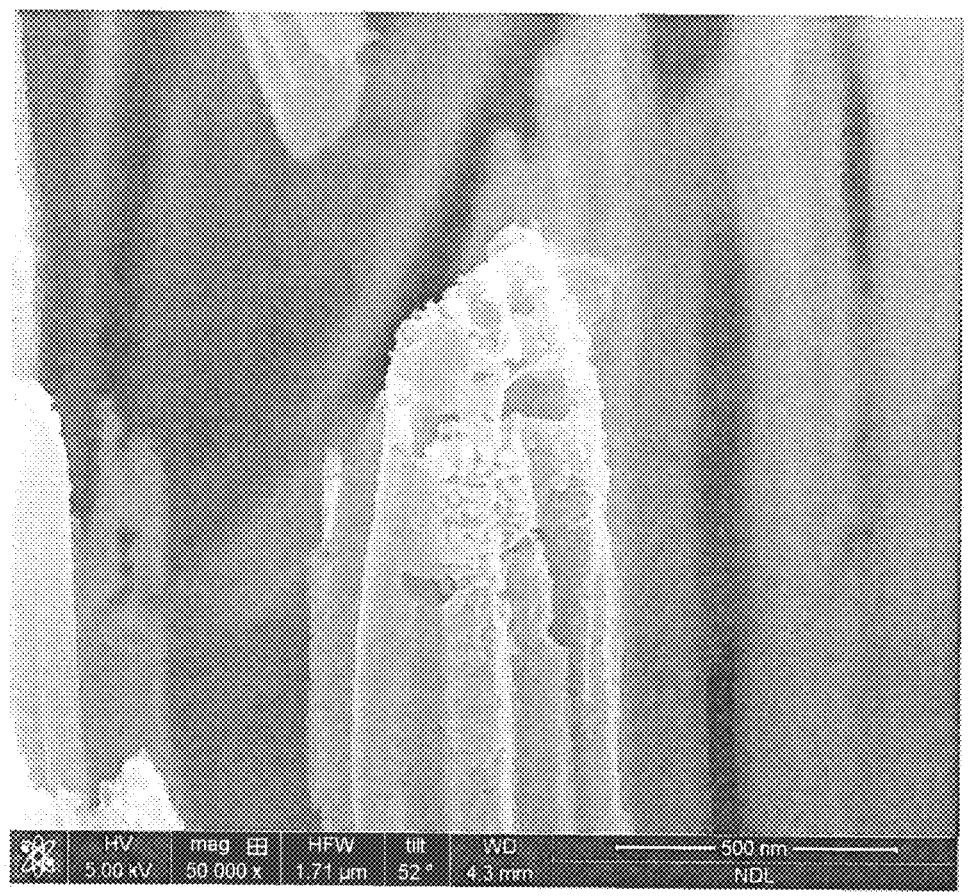
FIG. 9 is another SEM image (50,000×) of the discrete nano-sized structures.

An example of the discrete nano-sized structures 121 formed by the aforesaid process in the embodiment is shown in FIGS. 8 and 9.

The layer of binding agent 123 is formed on the top end 130 of each of the discrete nano-sized structures 121 for capturing the target biological particles 6. The layer of binding agent 123 is made from a binding agent material which is capable of specific binding to the target biological particles 6 to be captured and which may be an antigen material, an antibody material, a peptide material, a protein material, or combinations thereof. In order to enhance a capturing effect for the layer of binding agent 123, the target biological particles 6 to be captured may be bound to a biotinylated antibody, and the layer of binding agent 123 is made from a streptavidin material which has a specific binding interaction with biotin. The layer of binding agent 123 is formed by silylation of the discrete nano-sized structures 121 obtained in step c), followed by coating of the binding agent material on the top end 130 of each of the discrete nano-sized structures 121.

The pores 122 in the top end 130 of each of the discrete nano-sized structures 121 may be formed by, for example, extension of an etching period such that the specific surface area of the top end 130 of each of the discrete nano-sized structures 121 may be increased, which in turn increases the surface area of the layer of binding agent 123 formed on the top end 130 of each of the discrete nano-sized structures 121 so as to increase a binding effect of the layer of binding agent 123. In addition, the induced charges gathered on the top end 130 of each of the discrete nano-sized structures 121 may also be increased due to such increased specific surface area so as to further increase the effect for capturing the target biological particles 6.

Figure 7:
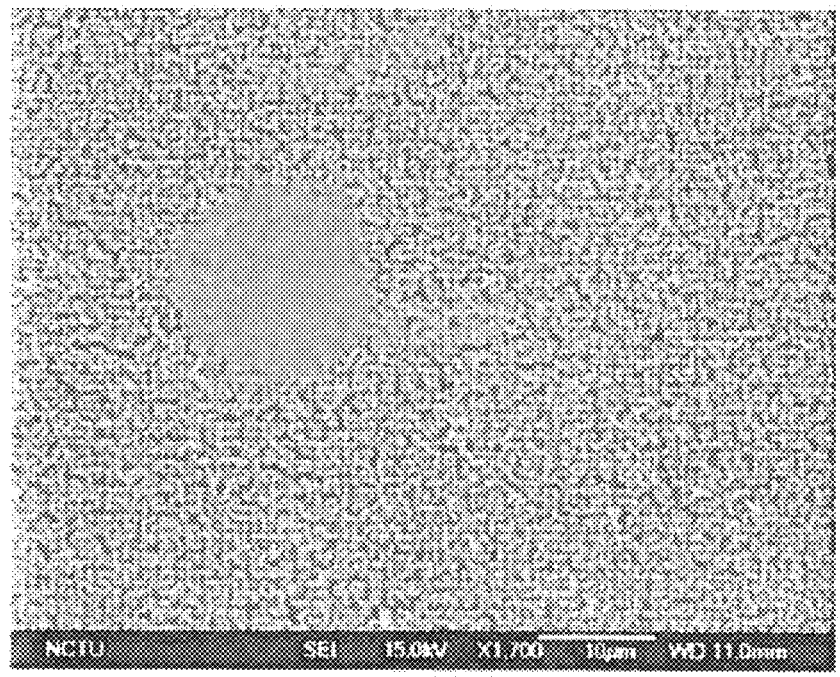
FIG. 7 is a scanning electron microscope image of the monolithic chip in which a target biological particle is captured.

The electrode unit 2 includes a first electrode 21 disposed on the lower major surface 1111 of the lower cell body 111, and a second electrode 22 disposed on the top major surface 1121 of the upper cell body 112. In order to enhance moving of the target biological particles 6 contained in the liquid sample toward the layer of binding agent 123 and to prevent undesirable materials contained in the liquid sample from depositing on the layer of binding agent 123, the first electrode 21 and the second electrode 22 are alternatively applied with a voltage during passage of the liquid sample through the fluid passage 10 so as to permit the capturing device 1 to be switched between a capturing mode and a non-capturing mode. In the capturing mode, a non-uniform electric field is produced between the first electrode 21 and the second electrode 22 to permit dielectrophoresis to occur such that the target biological particles 6 and the undesirable materials contained in the liquid sample are attracted by the dielectrophoretic force to move toward the layer of binding agent 123 and that the target biological particles 6 are bound to the layer of binding agent 123 accordingly, as shown in FIG. 7. In the non-capturing mode, a non-uniform electric field opposite to that produced in the capturing mode is produced between the first electrode 21 and the second electrode 22 to result in a dielectrophoretic force in a direction opposite to that generated in the capturing mode such that the undesirable materials contained in the liquid sample move away from the layer of binding agent 123 while the target biological particles 6 remain bound to the layer of binding agent 123. The target biological particles 6 may be effectively bound to and concentrated on the layer of binding agent 123 accordingly after several switching cycles. In a variation of the embodiment in which the second electrode 22 is not disposed on the cell structure 11, the first electrode 21 is applied with an electric current such that the lower cell body 111 and the monolithic chip 12 are electrically polarized to produce electric dipole moment so as to permit the target biological particles 6 to be bound to the layer of binding agent 123.

The signal measuring module 3 includes a signal determining device 32, and a first metal conductor 31 and a second metal conductor 33 which are disposed on the lower adjoining surface 1112, which extend in the longitudinal direction, and which are spaced apart from each other by the lower recess 101. Each of the first metal conductor 31 and the second metal conductor 33 has two opposite end portions 311, 331 electrically connected to the signal determining device 32.

Before the biological detection system according to the disclosure is used for detecting a liquid sample containing the target biological particles 6, a pair of measuring signals are supplied from the signal determining device 32 to one end portion 311 of the first metal conductor 31 and one end portion 331 of the second metal conductor 33, respectively, and a pair of feedback signals are received by the signal determining device 32 from the other one end portion 311 of the first metal conductor 31 and the other one end portion 331 of the second metal conductor 33, respectively. The feedback signals as received are taken as background signal data.

The biological detection system according to the disclosure is then used for detecting a liquid sample containing the target biological particles 6 by repeating the aforesaid procedure to receive another pair of feedback signals, which are taken as variation signal data. Substantial signal data is obtained by subtracting the background signal data from the variation signal data. The number and type of the target biological particles 6 are analyzed via an immunefluorescence staining technique combined with fluorescence microscopy. A series of liquid samples containing various numbers of the target biological particles 6 are detected via the aforesaid procedure to construct a database.

Thereafter, a liquid sample containing the target biological particles 6 to be determined may be detected via the aforesaid procedure to obtain variation signal data, which is compared to the data in the database to determine the number and type of the target biological particles 6.

The signal determining device 32 included in the embodiment is a vector network analyzer which uses a differential signal as the measuring signal.

Figure 4:
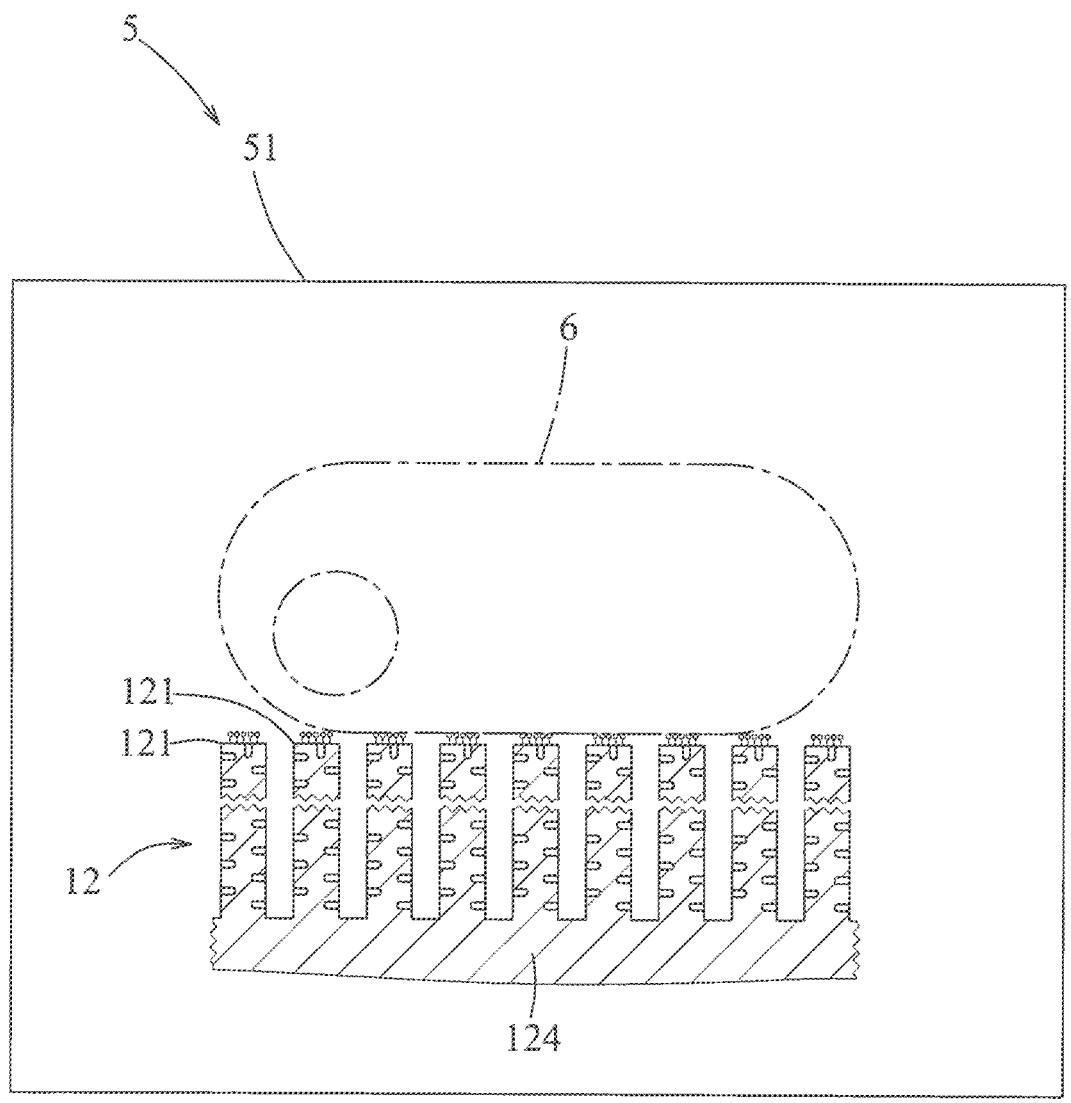
FIG. 4 is a schematic sectional view of the monolithic chip in a state in which a plurality of discrete nano-sized structures included in the monolithic chip are broken via oscillation of an oscillator included in the first embodiment.

Specifically referring to FIG. 4, the separating device 5 is used for separating the discrete nano-sized structures 121 from the monolithic chip 12. The separating device 5 includes an oscillator 51 for oscillating the monolithic chip 12 to break the discrete nano-sized structures 121 so as to separate the discrete nano-sized structures 121 from the cell structure 11. In the embodiment, the oscillator 51 is an ultrasonic oscillator. Since the discrete nano-sized structures 121 has a weakened mechanical strength as a result of the pores 122 formed in the exterior surface 120 thereof, they may be easily broken by the oscillator 51.

Referring to FIGS. 1 and 4 again, when the biological detection system according to the disclosure is used for detecting the liquid sample containing a plurality of the target biological particles 6, the flow stream of the liquid sample may be deflected by the baffles 131 while the liquid sample flows through the fluid passage 10 so as to result in the turbulent effect for the liquid sample in the fluid passage 10 to enhance the contact of the target biological particles 6 with the layer of binding agent 123 formed on the top end 130 of each of the binding the discrete nano-sized structures 121. At the same time, the first electrode 21 and the second electrode 22 of the electrode unit 2 are alternatively applied with a voltage during passage of the liquid sample through the fluid passage 10 to permit the capturing device 1 to be switched between a capturing mode and a non-capturing mode such that the target biological particles 6 may be effectively bound to and concentrated on the layer of binding agent 123. The target biological particles 6 captured on the layer of binding agent 123 may be measured by the signal measuring module 3. Finally, the discrete nano-sized structures 121 capturing the target biological particles 6 may be separated from the monolithic chip 12 using the separating device 5 after the measurement.

Figure 5:
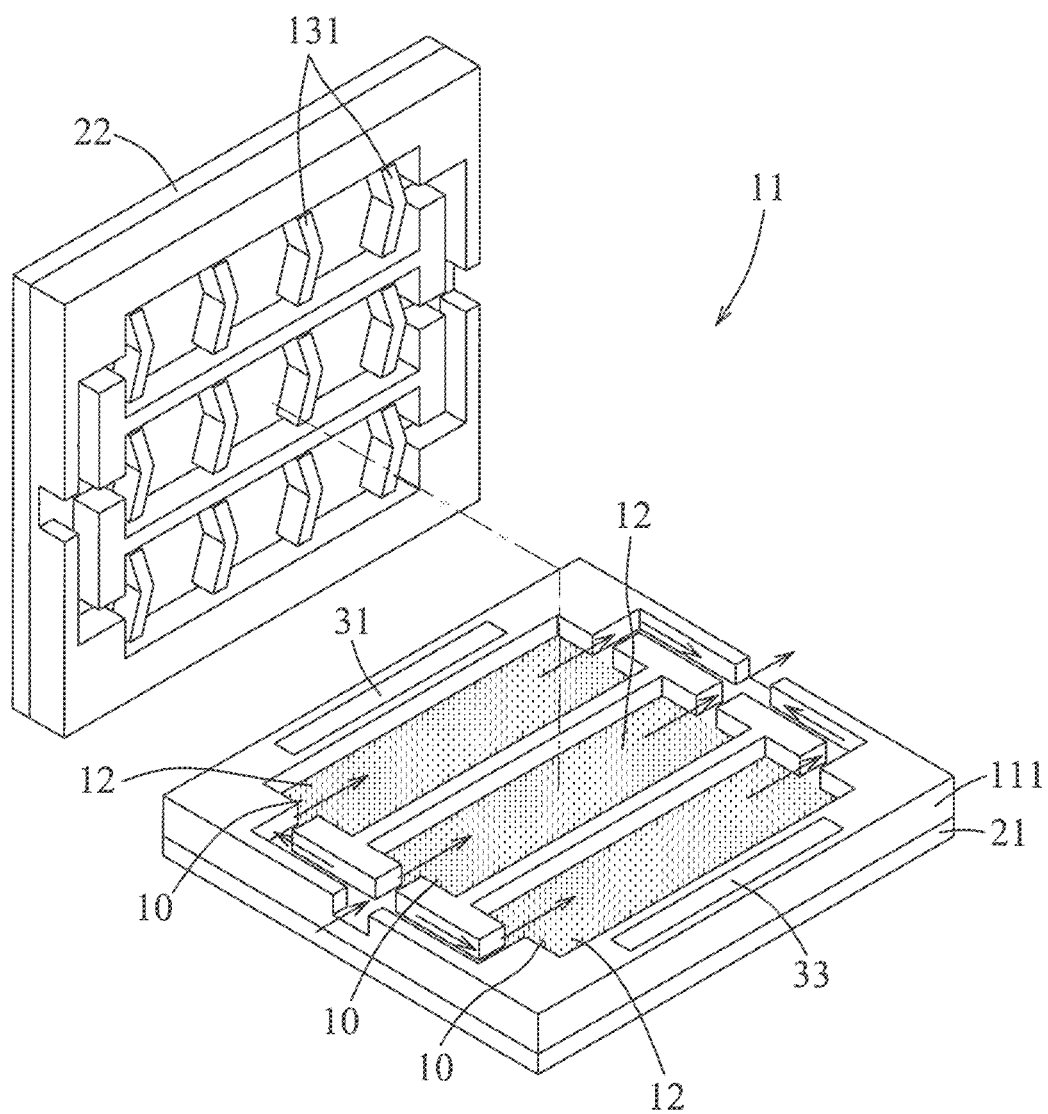
FIG. 5 is a schematic perspective view of a second embodiment of a biological detection system according to the disclosure.

Referring to FIG. 5, a second embodiment of a biological detection system according to the present disclosure is shown to be similar to the first embodiment except that in the second embodiment, the cell structure 11 defines a plurality of the fluid passages 10 and a plurality of the monolithic chips 12 are included and disposed in the fluid passages 10 correspondingly.

Figure 6:
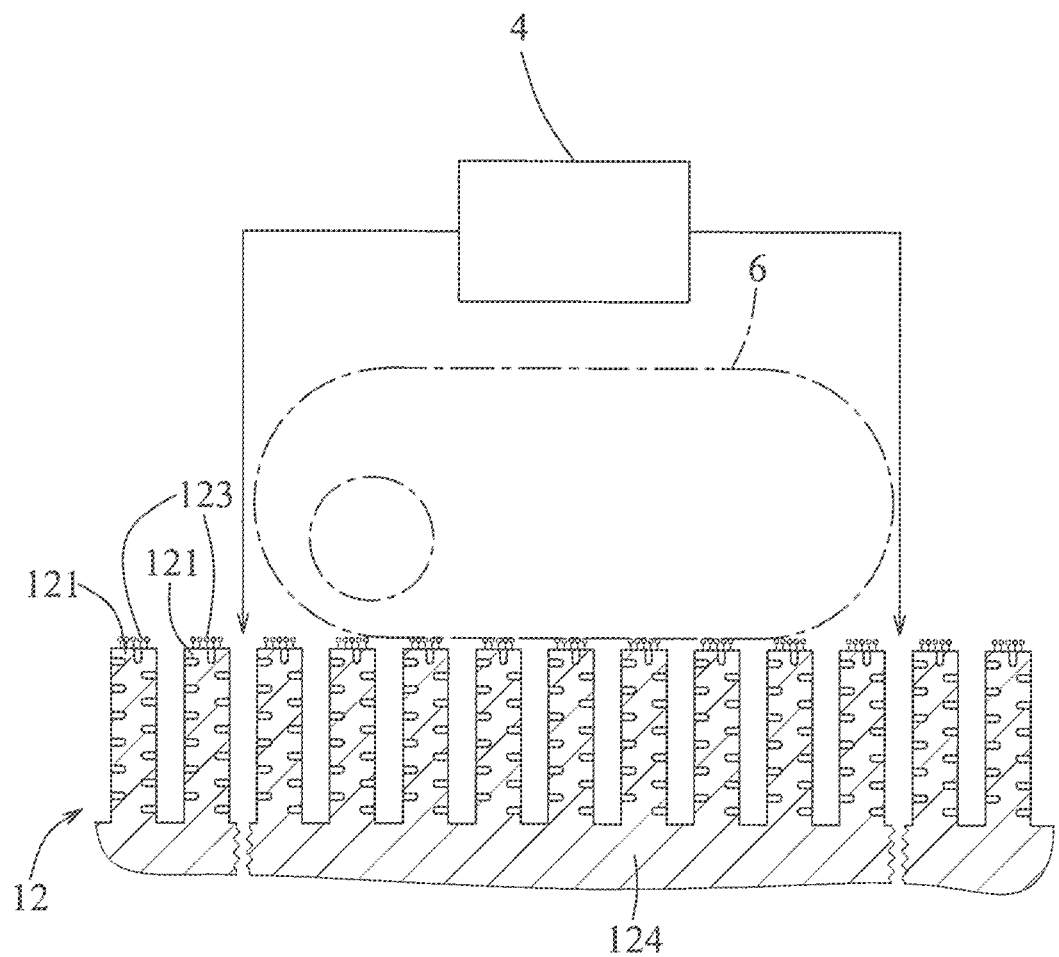
FIG. 6 is a schematic sectional view of the monolithic chip in a state in which the discrete nano-sized structures included in the monolithic chip are separated via cutting of a cutter included in the first embodiment.

With reference to FIG. 6, the first and second embodiments may further include a cutter 4 disposed upstream of the separator 5 to separate the portion of the monolithic chips 12 capturing the target biological particles 6 from the cell structure 11. A non-limiting example of the cutter 4 is an ultraviolet laser cutter. The portion of the monolithic chips 12 cut by the cutter 4 is then oscillated by the oscillator 51 to separate the discrete nano-sized structures 121 capturing the target biological particles 6 from the monolithic chips 12.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A biological detection system adapted for detecting a liquid sample containing a plurality of target biological particles, comprising:
    a capturing device including
        a cell structure including
            a lower cell body having
                a lower major surface, and
                a lower adjoining surface opposite to said lower major surface in a transverse direction and having a lower recess which extends downwardly to terminate at an inner floor surface, the lower recess including an upper sub-recess configured to permit passage of the liquid sample and a lower sub-recess, and
            an upper cell body having
                a top major surface, and
                an upper adjoining surface which is opposite to said top major surface in the transverse direction, the upper adjoining surface having an upper recess extending toward said top major surface to terminate at a ceiling surface and configured to permit passage of the liquid sample;
        an inlet disposed upstream of said lower recess for introducing the liquid sample into said upper sub-recess of said lower recess;
        an outlet disposed downstream of said lower recess and opposite to said inlet in a longitudinal direction;
        a monolithic chip configured to be matingly fitted in said lower sub-recess and including a substrate and a plurality of discrete nano-sized structures which are displaced from each other in the longitudinal direction, each of the discrete nano-sized structures extending uprightly from said substrate to terminate at a top end; and
        a layer of binding agent formed on said top end of each of said discrete nano-sized structures for capturing the target biological particles; and
    a signal measuring module including:
        a signal determining device; and
        a first metal conductor and a second metal conductor which are disposed on the lower adjoining surface, which extend in the longitudinal direction, and which are spaced apart from each other by the lower recess, each of the first metal conductor and the second metal conductor having two opposite end portions electrically connected to the signal determining device.

2. The biological detection system according to claim 1, wherein said discrete nano-sized structures are formed by a process including steps of:
    a) providing an etchable layer on said substrate;
    b) masking a plurality of areas on the etchable layer, each of the areas corresponding to the top end of each of the discrete nano-sized structures; and
    c) etching a plurality of unmasked areas of the etchable layer downwardly toward the substrate so as to form the discrete nano-sized structures.

3. The biological detection system according to claim 2, wherein step b) includes sub-steps of:
    b1) applying a layer of photoresist onto the etchable layer;
    b2) subjecting the layer of the photoresist to radiation exposure via a patterned mask and to development to form a patterned layer of the photoresist on the etchable layer so as to define the unmasked areas on which the photoresist is not provided;
    b3) forming a layer of silver catalyst on the unmasked areas; and
    b4) lifting off the patterned layer of the photoresist to leave the silver catalyst on the unmasked areas of the etchable layer.

4. The biological detection system according to claim 3, wherein step c) includes sub-steps of:
    c1) immersing the etchable layer obtained in sub-step b4) in an etchant aqueous solution containing HF and $H_2O_2$ to subject the unmasked areas of the etchable layer to a silver-catalyzed chemical etching reaction which etches downwardly toward the substrate to form the discrete nano-sized structures having a weakened mechanical strength as a result of a concurrent lateral etching; and c2) removing the silver catalyst from the etchable layer.

5. The biological detection system according to claim 2, wherein the etchable layer is made from a material selected from the group consisting of a semiconducting material, a biologically compatible material, and a combination thereof.

6. The biological detection system according to claim 5, wherein the semiconducting material is a silicon material.

7. The biological detection system according to claim 5, wherein the biologically compatible material is selected from the group consisting of polydimethylsiloxane, polymethyl methacrylate, polycarbonate, and combinations thereof.

8. The biological detection system according to claim 2, wherein the etchable layer is formed integrally with the substrate.

9. The biological detection system according to claim 1, wherein said discrete nano-sized structures are arranged in array.

10. The biological detection system according to claim 4, wherein each of said discrete nano-sized structures has an exterior surface which extends between said top end and said substrate and which is formed with a plurality of pores as a result of the concurrent lateral etching.

11. The biological detection system according to claim 10, wherein each of said pores has a size ranging from 500 pm to 50 nm.

12. The biological detection system according to claim 1, wherein said monolithic chip is formed integrally with said lower cell body.

13. The biological detection system according to claim 1, wherein said inlet includes a lower inlet half formed in said lower cell body, and an upper inlet half formed in said upper cell body and configured to be mated with said lower inlet half.

14. The biological detection system according to claim 1, wherein said outlet includes a lower outlet half formed in said lower cell body, and an upper outlet half formed in said upper cell body and configured to be mated with said lower outlet half.

15. The biological detection system according to claim 1, wherein said upper cell body further has a plurality of baffles disposed on said ceiling surface and displaced from each other in the longitudinal direction to deflect the flow stream of the liquid sample.

16. The biological detection system according to claim 1, further comprising an electrode unit which includes a first electrode disposed on one of said lower major surface of said lower cell body and said top major surface of said upper cell body.

17. The biological detection system according to claim 16, wherein said electrode unit further includes a second electrode disposed on the other of said lower major surface of said lower cell body and said top major surface of said upper cell body.

18. The biological detection system according to claim 1, further comprising a separating device for separating said discrete nano-sized structures from said monolithic chip.

19. The biological detection system according to claim 18, wherein said separating device includes an oscillator for oscillating said monolithic chip to break said discrete nano-sized structures.

* * * * *